United States Patent

Metz-Stavenhagen et al.

Patent Number: 5,476,464
Date of Patent: Dec. 19, 1995

[54] DEVICE FOR SETTING A SPINE

[75] Inventors: Peter Metz-Stavenhagen, Bad Wildungen; Bernd Robioneck, Shellhorn, both of Germany

[73] Assignee: Howmedica GmbH, Schoenkirchen, Germany

[21] Appl. No.: 198,246

[22] Filed: Feb. 18, 1994

[30] Foreign Application Priority Data

Feb. 25, 1993 [DE] Germany .............. 9302700 U

[51] Int. Cl.⁶ .................................. A61B 17/70
[52] U.S. Cl. .................................. 606/61; 606/73
[58] Field of Search ............... 606/61, 72, 73, 606/54, 59, 60

[56] References Cited

U.S. PATENT DOCUMENTS

| | | | |
|---|---|---|---|
| 5,176,678 | 1/1993 | Tsou ........................... | 606/61 |
| 5,207,678 | 5/1993 | Harms et al. ............... | 606/61 |

FOREIGN PATENT DOCUMENTS

| | | |
|---|---|---|
| 0330881 | 9/1989 | European Pat. Off. . |
| 9101115 | 2/1991 | WIPO . |
| 91/16020 | 10/1991 | WIPO .................... 606/61 |
| 9203100 | 3/1992 | WIPO . |

*Primary Examiner*—Tamara L. Graysay
*Attorney, Agent, or Firm*—Peter C. Richardson; Lawrence C. Akers; Elizabeth O. Slade

[57] ABSTRACT

The present invention relates to a device for setting a spine having damaged vertebrae, comprising an anchoring element including a shaft portion (16) to be attached to spaced vertebrae, the free end of said anchoring element including a slot (24) for receiving a distracting or, respectively, compressing bar (40) and a cap nut (42) to be screwed onto an outer thread (32) provided in the region of the receiving slot to urge an axial fixing portion (44) towards the bar received in said receiving slot. The invention is defined in that the receiving slot (24) is formed in a separate swivel head (20) including an inner end in the shape of a ball receiving portion (23) which has an aperture (28) through which said shaft portion (16;52) of the anchoring element (10;50) extends, wherein the diameter of the shaft portion adjacent said aperture is smaller than that of said aperture (28), and that a ball head (14;56) is provided at the end of the shaft portion (16;52), said ball head having a diameter larger than that of said aperture (28) and said ball head (14;56) in the ball receiving portion (23) entering the terminal region of said receiving slot (24).

13 Claims, 1 Drawing Sheet

DEVICE FOR SETTING A SPINE

The present invention relates to a device for setting damaged vertebrae in a spine.

BACKGROUND OF THE INVENTION

It is known to stabilize a spine having damaged vertebrae by implanting a stabilizing system in the vertebrae on either side of a damaged vertebra. For this, the spine is first set and then stabilized. It is further generally known to turn so-called pedicle screws into the pedicles of vertebrae and to connect the pedicle screws to each other through a more or less rigid connecting system. For example, this can be obtained by using a so-called distracting or compressing bar which is inserted in a receiving slot provided in the heads of the pedicle screws. The bar is usually provided with a thread, a grooving or some other surface roughness such that it can be fixed in the head of the pedicle screws by means of an appropriate locking means. EP 0 348 272 discloses a pedicle screw having a receiving slot which is provided with a thread to receive a locking screw. The locking screw fixes the distracting or compressing bar in the slot. U.S. Pat. No. 4,763,644 discloses a pedicle screw, the head of which is provided with an outer thread onto which a cap-shaped nut can be screwed. By means of a pin portion inserted into the receiving slot, the cap nut urges the bar against the bottom of the receiving slot. French patent 26 24 270 discloses a cap nut including a locking screw to fix the distracting or compressing bar in the receiving slot. Cap nuts have the advantage of holding together the legs of the slotted pedicle screw head. As mentioned above, there is a danger that the legs may spread apart, thus loosening the locking screw when a solid screw is screwed into the receiving slot. Furthermore, fixing of the distracting bar is risky. In the process of the operation, the pedicle screws are first secured. The position of the pedicle screws (or, respectively, the heads thereof) is optional to some extent, in particular, when the vertebrae are more or less displaced. According to the prior art it is required to prebend the distracting or compressing bar to be received in the receiving slots of the pedicle screws. Since the distracting and compressing bars must be stiff by nature, the process described requires the surgeon to apply substantial efforts, and the process is complicated.

An object of the present invention is to provide a device for setting a spine having damaged vertebrae so that there is reduced need for bending a distracting or compressing bar when the bar must be received and fixed in receiving slots of anchoring elements secured to the vertebrae when displaced vertebrae exist.

This object is solved by the device of the invention.

SUMMARY OF THE INVENTION

According to the invention, the receiving slot is formed in a separate swivel head including an inner end which is in the shape of a ball-receiving portion. The ball-receiving portion has an aperture through which the shaft portion of the anchoring element extends, wherein the diameter of the shaft portion adjacent the aperture is smaller than that of the aperture. A ball head is provided at the end of the shaft portion, the ball head having a diameter larger than that of the aperture. The ball head extends up to the terminal region of the receiving slot.

According to the invention, the anchoring element on the one hand and the swivel head on the other can take an angular position with respect to each other. Accordingly, the bar can be bent less and this is true for the saggital as well as the lateral setting direction.

When the anchoring element is represented by a pedicle screw, the latter need not be completely screwed into the vertebra. Rather, the inserted bar can be fixed by means of the cap nut after an initial screwing operation. Subsequently the pedicle screw can be rotated about its shaft to either pull a dislocated vertebra rearwards or sidewards when the instrumentation is performed from anterior. After repositioning a luxated vertebra (trauma, degenerative change or olisthesis) the bar can be compressed or distracted to obtain a further lordosizing or kyphosizing, eliminating the need of bending the bar. Thereafter the cap nut is tightened, whereby the axial fixing portion secures the bar with respect to the ball head to fix all parts in the axial and rotational direction. As mentioned before, a pedicle screw may be used as the anchoring element. Alternatively, a hook can be provided which acts beyond an extension of the vertebra, for example. The ball head of the anchoring element can be formed separately with respect to the anchoring element. However, an integral structure of ball head and anchoring element is preferred.

In a preferred embodiment the axial fixing portion as well is integrally formed on the cap nut.

In particular, the swivel head is shaped to have minimal outer dimensions, if possible, while maintaining sufficient stability and eliminating distinct projections or edges.

According to a further aspect of the invention, the end region of the swivel head facing the connecting element is tapered, the tapered section being followed by a radial shoulder and a cylindrical portion, wherein the outer diameter of the nut approximately corresponds to the outer diameter of the shoulder.

BRIEF DESCRIPTION OF THE DRAWING

The invention will now be described with reference to the accompanying drawing which shows.

DESCRIPTION OF THE PREFERRED EMBODIMENT

Figure 1:
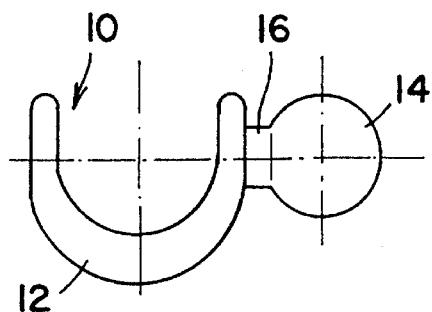
FIG. 1 a side view of a hook provided for the device according to the invention.
Figure 2:
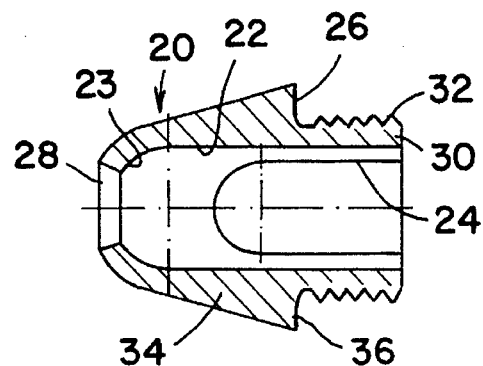
FIG. 2 a section of a swivel head of the device according to the invention.

A hook 10, a so-called laminar hook, for example, comprises a hook portion 12, a ball head 14 and a shaft portion 16 located between the hook portion 12 and the ball head 14. A swivel head 20 as shown in FIG. 2 comprises a dead end bore 22 which is ball-shaped at the bottom 24. Diametrically opposed slots 24 extend from the free end, which slots end at a distance from the bottom of the dead end bore as indicated at 26. The bottom of the bore 22 is provided with a central aperture 28 tapering outwardly.

The portions 30 which are left between the slots 24 of the swivel head 20 are provided with an outer thread 32.

Extending from the aperture 28, the swivel head 20 is formed to include a conical section 34 ending in a radial shoulder 36. The thread 32 is terminated at the radial shoulder 36.

Figure 3:
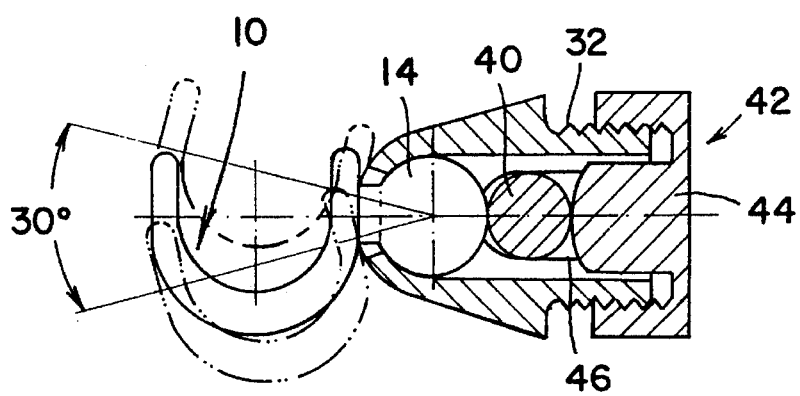
FIG. 3 the assembly of the hook of FIG. 1 and the swivel head of FIG. 2 in combination with a distracting bar.

As FIG. 3 shows, the ball head 14 of the hook 10 is received in the ball receiving portion 24 of the swivel head 20. Since the shaft portion 16 has a smaller diameter than that of the aperture 28, the hook can perform a pivoting motion up to a maximum of 30°. This is indicated in FIG. 3 by dashed lines.

When the hook portion 12 cannot be inserted through the aperture 28 from the free end of the bore 22, the hook portion 12 and the ball head 14 including the shaft portion 16 can be shaped in two parts which are screwed to each other, for example.

FIG. 3 further shows a distracting or compressing bar 40, extending through the slots 24. A cap nut 42 is screwed on the outer thread 32 of the swivel head 20. An axial fixing portion 44 integrally formed on the nut 42 includes a rounded end 46 suited to engage the bar 40. Since the diameter of the ball 14 is larger than the distance between the ball receiving portion and the end 26 of the slot 24, the bar 40 is urged towards the ball head 14 when the nut is screwed on the thread 32 and when the fixing portion 44 is urged to press against the bar 40 from outside. Before the fixing step is performed, the ball head 14 and the bar 40 can be positioned in different angular positions. It is thus not necessary to bend the bar 40 when different angular positions due to the position of each vertebra have to be negotiated while inserting the bar 40.

Figure 4:
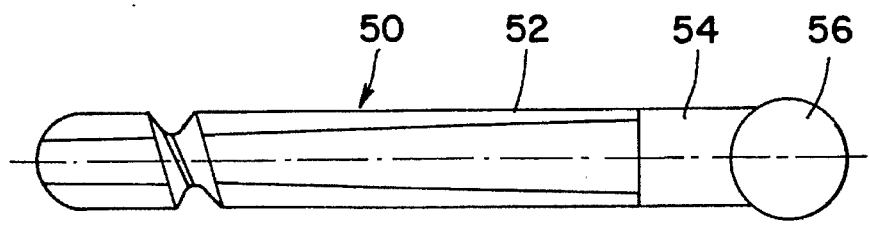
FIG. 4 a pedicle screw which can be used in an alternative embodiment of FIG. 3, instead of a hook.

FIG. 4 shows a pedicle screw 50 comprising a threaded shaft 52 followed by a threadless shaft portion 54 ending in an integral ball head 56. The dimension of the shaft 52 is selected to be placed through the aperture 28 of the swivel head 20, while the ball head 56 is received in the ball receiving portion 24. Like the hook 10, the pedicle screw 50 can take any angular position within limits.

The shaft portion 54 is preferably provided with tool engaging surfaces to rotate the pedicle screw 50, while the ball head 56 sits in the ball receiving portion 24. Accordingly, it is possible to relocate a luxated vertebra.

It is further noted that the nut 42 can be provided with tool engaging surfaces, for example a pair of diametrically opposite flats.

We claim:

1. A device for setting a spine having damaged vertebrae, comprising: an anchoring element including a shaft portion to be attached to spaced vertebrae, and having a free end including a slot for receiving a distracting and compressing bar, and a cap nut having an axial fixing portion, said nut to be screwed onto an outer thread provided in the region of said slot so as to urge said axial fixing portion towards said bar received in said receiving slot, wherein the receiving slot is formed in a separate swivel head including an inner end in the shape of a ball receiving portion which has an aperture through which said shaft portion of the anchoring element extends, wherein the diameter of the shaft portion adjacent said aperture is smaller than that of said aperture, and wherein a ball head is provided at the end of the shaft portion, said ball head having a diameter larger than that of said aperture and said ball head in the ball receiving portion entering said inner end of said receiving slot.

2. The device of claim 1, wherein the ball head is formed integral with the anchoring element.

3. The device of claim 2, wherein the ball receiving portion of the swivel head includes a spherical surface.

4. A device for setting a spine having damaged vertebrae, comprising: an anchoring element including a shaft portion to be attached to spaced vertebrae and having a free end including a slot for receiving a distracting and compressing bar, and a cap nut having an axial fixing portion, said nut to be screwed onto an outer thread provided in the region of said slot so as to urge said axial fixing portion towards said bar received in said receiving slot, wherein the receiving slot is formed in a separate swivel head including an inner end in the shape of a ball receiving portion which has an aperture through which said shaft portion of the anchoring element extends, wherein the diameter of the shaft portion adjacent said aperture is smaller than that of said aperture, and wherein a ball head is provided at the end of the shaft portion, said ball head having a diameter larger than that of said aperture and said ball head in the ball receiving portion entering said inner end of said receiving slot, wherein the axial fixing portion is formed integral with the nut.

5. The device of claim 4, wherein the axial fixing portion has a rounded free end.

6. The device of claim 5, wherein the interior surface of said inner end of the swivel head facing towards the anchoring element is ball-shaped.

7. The device of claim 6, wherein the exterior surface of said inner end of the swivel head facing towards the anchoring element is tapered and forms a conical section, said conical section merging into a cylindrical portion via a radial shoulder and wherein the outer diameter of the nut approximates the outer diameter of said shoulder.

8. A device for setting a spine having damaged vertebrae, said device to be used in conjunction with a spine stabilizing bar and comprising:
 a) an anchoring element to be attached to a vertebra, said anchoring element having:
  1) a shaft portion having a first end and a second end;
  2) a ball head located at said first end; and
  3) an anchoring part located at said second end, said anchoring part being selected from the group consisting of a lamina hook and a pedicle screw;
 b) a separate swivel head having a lateral exterior surface and having:
  1) a first swivel head end in which said ball is located, and can rotate, said first swivel head end having an aperture therein through which said shaft portion extends and can rotate;
  2) a second swivel head end having screw threading located on said lateral exterior surface thereof; and
  3) a first slot and a second slot located diametrically opposite each other on said lateral exterior surface and for receiving said spine stabilizing bar; and
 (c) a cap nut having threading and being suitable for being screwed onto said screw threading of said second end of said swivel head, said cap nut having an inner end which can contact said spine stabilizing bar when said spine stabilizing bar extends through said first slot and said second slot.

9. A device according to claim 8, wherein said ball head is integral with said shaft portion and said anchoring part.

10. A device for setting a spine having damaged vertebrae, said device to be used in conjunction with a spine stabilizing bar and comprising:
 a) an anchoring element to be attached to a vertebra, said anchoring element having:
  1) a shaft portion having a first end and a second end;
  2) a ball head located at said first end; and
  3) an anchoring part located at said second end, said anchoring part being selected from the group consisting of a lamina hook and a pedicle screw;
 b) a separate swivel head having a lateral exterior surface and having:

1) a first swivel head end in which said ball is located, and can rotate, said first swivel head end having an aperture therein through which said shaft portion extends and can rotate;
2) a second swivel head end having screw threading located on said lateral exterior surface thereof; and
3) a first slot and a second slot located diametrically opposite each other on said lateral exterior surface and for receiving said spine stabilizing bar and (c) a cap nut having threading and being suitable for being screwed onto said screw threading of said second end of said swivel head, said cap nut having an inner end which can contact said spine stabilizing bar when said spine stabilizing bar extend through said first slot and said second slot and wherein said ball head is integral with said shaft portion and said anchoring part and wherein said first swivel head end has an interior spherical surface, and wherein said inner end of said cap nut comprises an axial fixing portion formed integral with said nut.

11. A device according to claim 10, wherein said axial fixing portion has a rounded free end.

12. A device according to claim 11, wherein the interior surface of said inner end of the swivel head facing towards the anchoring element is ball-shaped.

13. A device according to claim 12, wherein the exterior surface of said inner end of the swivel head facing towards the anchoring element is tapered and forms a conical section, said conical section merging into a cylindrical portion via a radial shoulder and wherein the outer diameter of the nut approximates the outer diameter of said shoulder.

* * * * *